United States Patent [19]

Haining

[11] Patent Number: 4,950,251

[45] Date of Patent: Aug. 21, 1990

[54] SIMPLIFIED RETRACTABLE NEEDLE SYRINGE

[76] Inventor: Michael L. Haining, 6731 Ashmore, Houston, Tex. 77069

[21] Appl. No.: 449,971

[22] Filed: Dec. 12, 1989

Related U.S. Application Data

[63] Continuation-in-part of Ser. No. 322,282, Mar. 13, 1989, abandoned.

[51] Int. Cl.[5] .............................................. A61M 5/32

[52] U.S. Cl. ..................................... 604/195; 604/110

[58] Field of Search ............... 604/195, 218, 210, 187, 604/198, 110

[56] References Cited

U.S. PATENT DOCUMENTS

| | | | |
|---|---|---|---|
| 4,675,005 | 6/1987 | Deluccia | 604/198 X |
| 4,747,830 | 5/1988 | Gloyer | 604/110 |
| 4,883,471 | 11/1989 | Braginetz et al. | 604/195 |

*Primary Examiner*—John D. Yasko

*Attorney, Agent, or Firm*—Richard L. Moseley

[57] ABSTRACT

A simplified retractable needle hypodermic syringe is provided which includes a barrel having a needle carrier mounted therein with a cannula attached thereto. A slidable plunger is mounted within the barrel which includes a shaft and hub for locking to the carrier. The plunger seal is conveniently mounted about the shaft between the plunger and the hub.

4 Claims, 3 Drawing Sheets

53
50
80
60
20
24
12
10
11
30
90
40

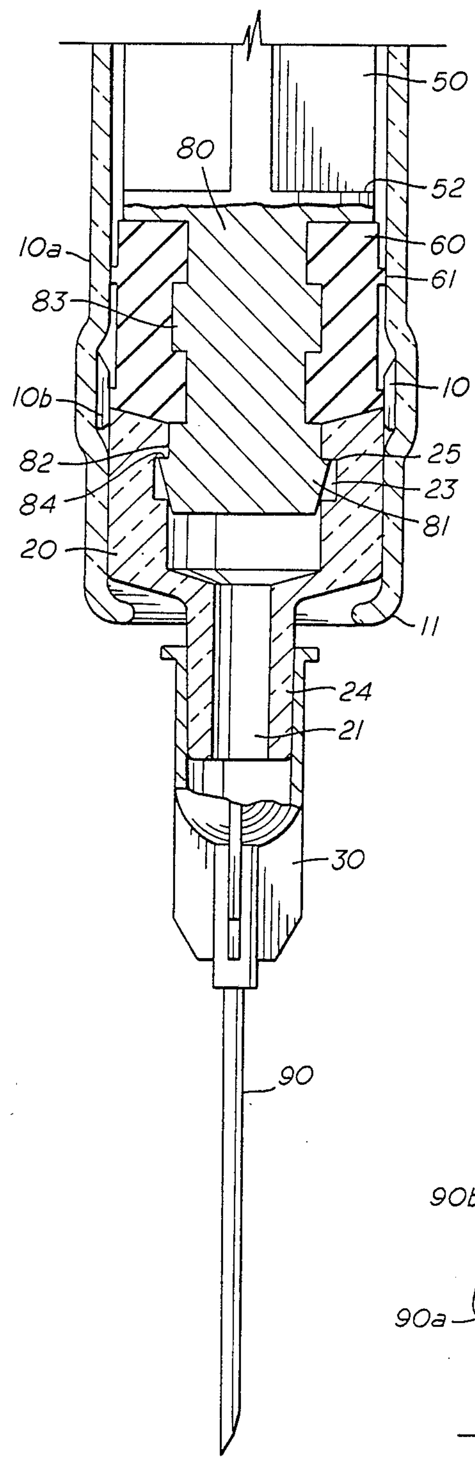
FIG. 4
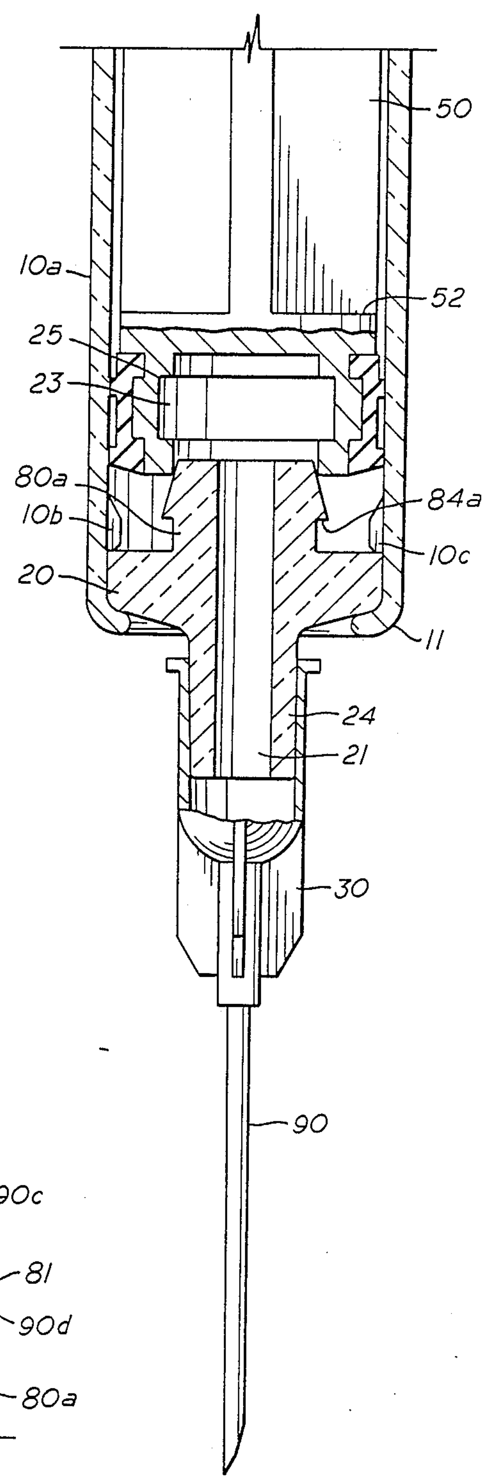
FIG. 5
90b
21
90c
81
90a
90d
80a
FIG. 6

SIMPLIFIED RETRACTABLE NEEDLE SYRINGE

BACKGROUND OF THE INVENTION

This application is a continuation in part of my earlier patent application Ser. No. 07/322,282 filed on Mar. 13, 1989 now abandoned.

Due to the recent advent of the AIDS virus, which may be contracted by contaminated hypodermic syringes, there have been several retractable needle hypodermic syringes invented and patented. The retraction of the needle into the barrel of the syringe after use reduces the risk of "needle prick", or the accidental pricking of the person giving the injection after the syringe has been used.

Some of the recently patented retractable needle syringes include U.S. Pat. Nos. 4,692,156 (Haller); 4,675,005 (DeLuccia); 4,747,830 (Gloyer, et al); and my own U.S. Pat. No. 4,790,822. While each of the patents disclose devices which would be suitable for use, none appears of simple enough construction for mass production at competitive costs. Generally each discloses a sophisticated locking or sealing mechanism for locking the needle carrier to the plunger or sealing the carrier in the barrel.

With the practical thought in mind that the hypodermic syringe is disposable and made for only one use, I have developed a simplified version of my earlier patented syringe which can be manufactured inexpensively and performs satisfactorily.

SUMMARY OF THE INVENTION

The simplified retractable needle hypodermic syringe of the present invention is designed to include the minimum number of parts and to utilize as much as possible from currently available syringe parts. The syringe comprises a hollow cylindrical barrel open at both ends with a finger flange at the upper end and an inwardly projecting lip at the lower end. A rigid needle carrier of hard plastic is seated within the barrel on the lip with a projection extending out of the barrel for attachment of a standard hypodermic needle or cannula (the words are used interchangeably herein). The only seal provided is by friction between the outer wall of the needle carrier and inner wall of the barrel and lip. A plunger is slidably mounted within the barrel which defines the fluid chamber. A shaft extends from the lower end of the plunger which terminates in a hub. The hub is adapted to fit and lock into an enlarged bore near the upper end of the carrier. The plunger seal conveniently fits around the shaft between the end of the plunger and the hub. The hub clicks and locks into the carrier after use, allowing the carrier and needle to be retracted into the barrel. Additionally, the hub may be broken off in the carrier blocking the fluid channel and preventing any further use of the syringe.

While the friction seal between the carrier and the barrel may lose its integrity after repeated movement in the barrel, it does provide a good seal for at least one use. It is the simplicity of the locking mechanism and the absence of any special sealing mechanism for the carrier which distinguishes the present invention from the prior art.

BRIEF DESCRIPTION OF THE DRAWING

FIG. 4 is a side elevational view in partial cross section of the lower end of a second embodiment of the syringe of the present invention.

FIG. 5 is a side elevational view in partial cross section of the lower end of a third embodiment of the syringe of the present invention.

FIG. 6 is a perspective view of an alternate hub which may be used in any of the embodiments of the present invention.

DETAILED DESCRIPTION OF THE PREFERRED EMBODIMENT

For a detailed description of the preferred embodiment the reader is directed to the accompanying figures in which like components are given like numerals for ease of reference.

Figure 1:
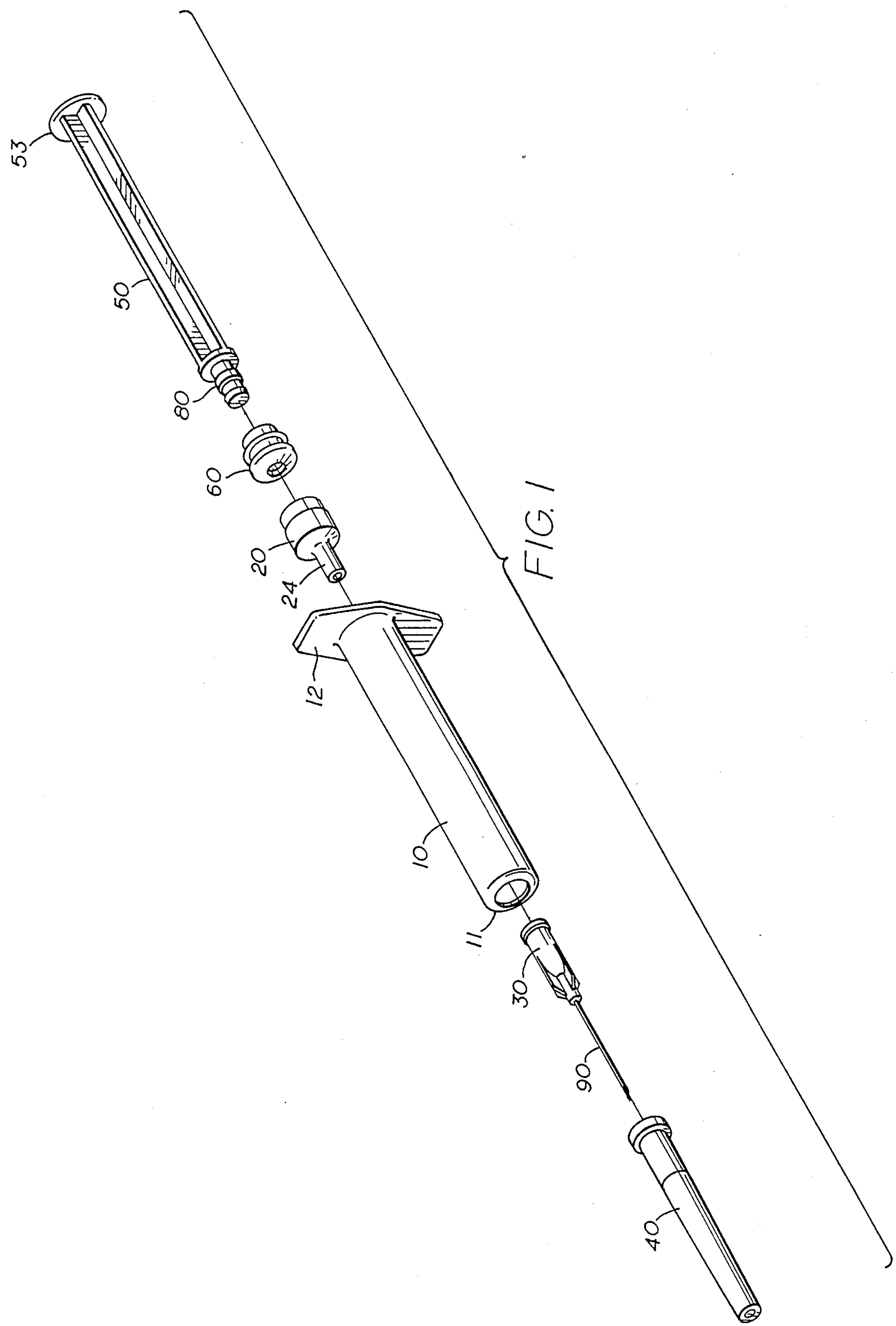
FIG. 1 is an exploded perspective view showing all of the parts of the retractable needle syringe of the present invention.

In FIG. 1 the simplicity of the present retractable needle hypodermic syringe is illustrated in an exploded view showing all of the components. The syringe is shown to comprise a hollow cylindrical barrel 10 with standard finger flanges 12 on one end and inwardly projecting lip 11 on the opposite end. A rigid needle carrier 20 of hard plastic is inserted into the barrel 10 through the flanged end opening and is seated on the lip 11 such that the extension 24 protrudes out of the barrel 10. A cannula 90 is attached to extension 24 by friction fit through sleeve 30 integral with cannula 90. The cannula is provided with protective sheath 40 for protection before use. Plunger 50 with shaft 80 about which is secured a rubber seal 60 is inserted into the barrel 10 and the syringe is ready for use. The entire syringe thus consists of only six distinct parts. Only the carrier and plunger are different from standard syringes once the needle mounting extension has been removed from the lower end of the barrel to provide lip 11. In one embodiment which has been made from an existing syringe, even the plunger seal has been reused.

Figure 2:
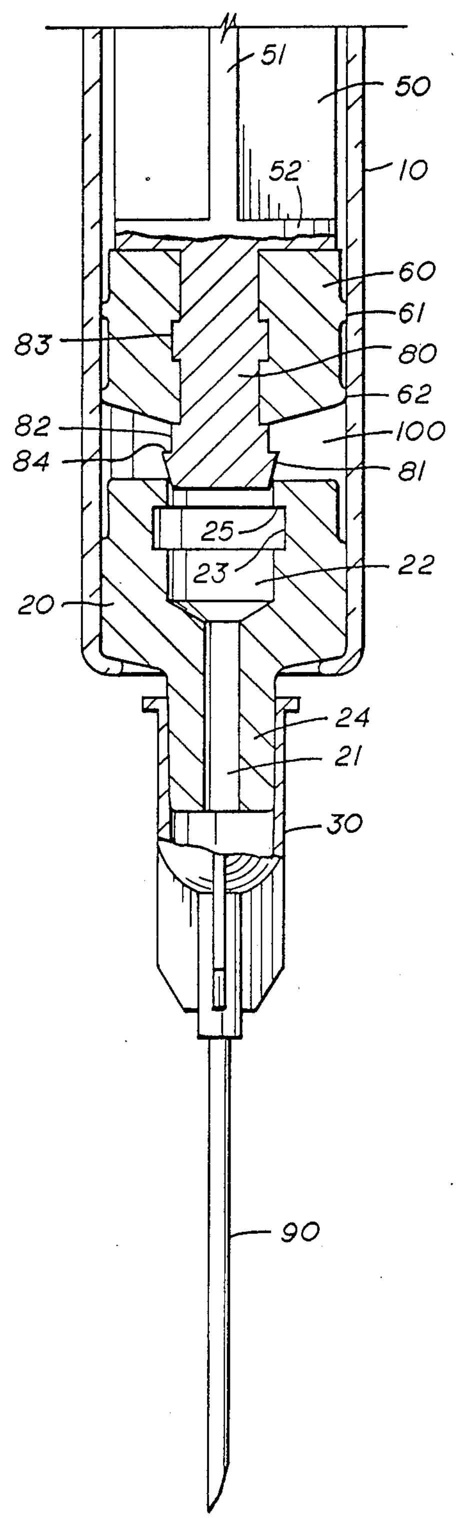
FIG. 2 is a side elevational view in partial cross section of the lower end of the assembled syringe of the present invention.

Referring now to FIG. 2 details of the new parts are illustrated. The carrier 20 is shown seated on the lip 11 with extension 24 protruding out of the barrel. The outer diameter of the carrier is sized to provide a snug friction seal with the inner walls of the barrel 10. Both the inner walls of the barrel 10 and the outer diameter of the carrier 20 are relatively smooth for ease of manufacture. Clearances may have to be adjusted for different material of construction to provide the seal while allowing the carrier to be retracted with minimum force. The integral sleeve 30 of cannula 90 is secured to extension 24 normally by a tight friction fit also. However additional securing means, such as an approved glue, may be used. A central bore 21 extends through the carrier 20 to provide fluid communication between the cannula 90 and fluid chamber 100. Near the upper end of central bore 21 is a hollow chamber 22 which includes an enlarged bore 23.

Plunger 50 is slidably mounted within barrel 10. Shaft 80 extends from the lower end 52 of the plunger 50. At the lower end of shaft 80 is a hub 81 which is adapted to fit and lock into enlarged bore 23 in carrier 20. Widened shoulders 82 and 83 are provided along shaft 80 to secure rubber seal 60 to the shaft between the plunger end 52 and hub 81.

Figure 3:
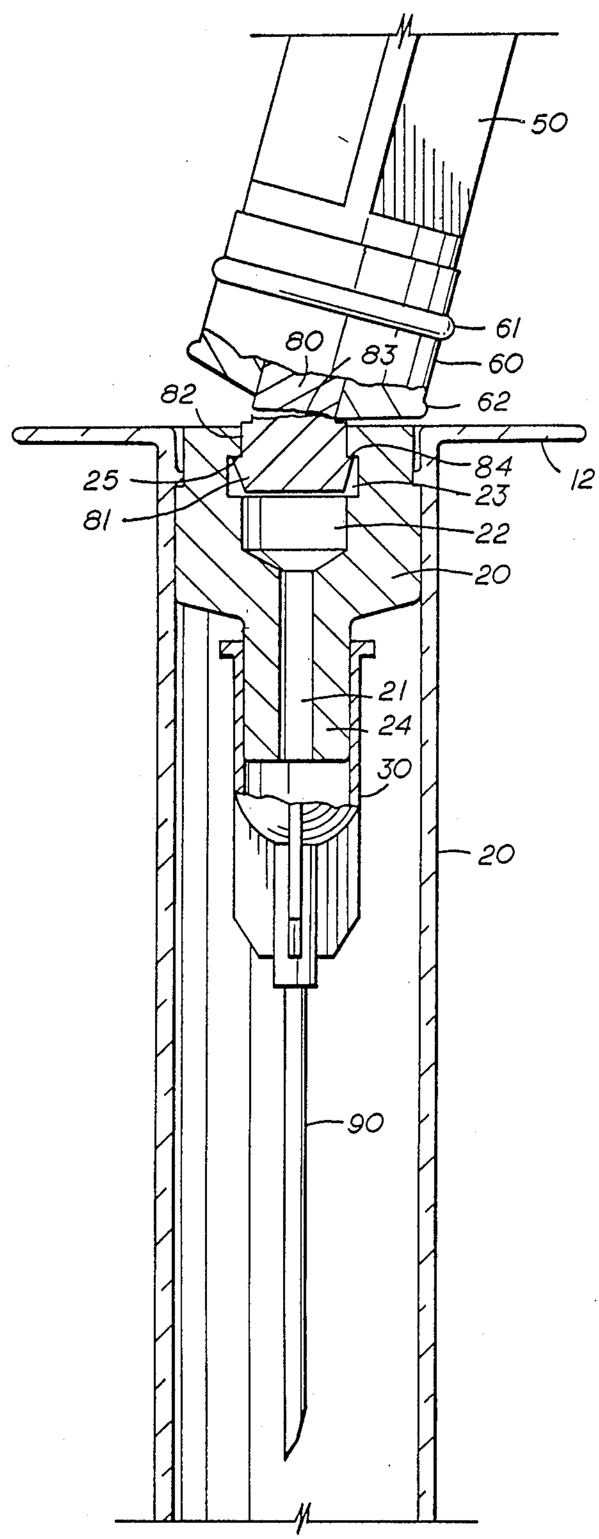
FIG. 3 is a side elevational view in partial cross section of the upper end of the assembled syringe with the needle retracted and hub broken.

Referring now to FIG. 3 the cannula 90 is shown retracted into the barrel 10. The hub is shown engaged within enlarged bore 23 with shoulder 84 in looking engagement with the upper inner surface 25 of enlarged bore 23. The shaft 80 is shearable above hub 81 so that the hub may be broken off inside the enlarged bore 23 effectively blocking fluid channel 21. Preformed perforations (not shown) may be provided to allow the shearing while still providing sufficient tensile strength to pull the carrier with cannula into the barrel.

In use the plunger 50 is depressed in the barrel 10 until solid resistance is met between the hub 81 and carrier 20 as shown in FIG. 2. The cannula 90 may then be inserted into the fluid to be injected and the fluid drawn into the chamber 100 by retraction of the plunger 50. Any air drawn in with the fluid may be removed in the usual manner—by inverting the syringe and thumping it until the bubble rises to the cannula end and depressing the plunger until fluid exits the cannula. The fluid may then be injected. As soon as the cannula is withdrawn from the recipient, the user may then further depress the plunger 50 until the hub 81 to engages the carrier 20. After the hub 81 has engaged the carrier 20 the needle carrier 20 with cannula 90 may then be retracted into the barrel 10. Finally, the hub 81 may be broken off of shaft 80 and left with the carrier 20 to prevent any further use of the syringe.

All of the materials of construction are conventional. For example, the barrel may be of transparent hard or soft plastic as is now commonly used in disposable syringes. The plunger and needle carrier are of hard plastic with the plunger seal being of standard rubber suitable for medical purposes.

If the barrel is of the soft deformable type plastic it may be preferred to have stops or shoulders above the needle carrier as disclosed in my earlier U.S. Pat. No. 4,790,822 which is incorporated herein by reference. Referring now to FIG.4 the shaft 80 with hub 81 and enlarged bore 23 disclosed herein replace the T type head and frusto-conical snap ring disclosed therein. Shoulders or stops 10 and 10b extend inwardly from the wall directly above the carrier 20 to provide additional securing means for the carrier. The plunger 50 is provided with the expansion means disclosed in my earlier patent to deform the walls when the hub 80 engages the enlarged bore 23 to allow retraction of the carrier 20.

Additionally, as shown in FIG.5 the shaft **80*a* and enlarged bore positions may be reversed with the central bore 21 of the carrier 20 extending through the shaft 80*a*. Longitudinal slots 90*a*-90*d* may be provided along the shaft 80*a* as shown in FIG.6 to provide some flexibility to the hub 81 and allow easy locking into the enlarged locking bore 23 on the lower end of the piston 50. If the shaft 80 is on the lower end of the piston as shown in FIG. 4, it may be hollow with the longitudinal slots 90*a*-90*d* continuing to provide flexibility for the hub 81. the flexibility allows the hub 80 or 80*a* to collapse inwardly as it enters the central bore and then spring outwardly as it enters the enlarged bore 23 for locking engagement by shoulders 84 or 84*a***.

What is claimed is:

1. A hypodermic syringe having a retractable needle, comprising:
   - a hollow cylindrical barrel of semi-rigid deformable plastic open at both ends and having an inwardly projecting lip at the lower end and finger flanges at the upper end;
   - a rigid cylindrical needle carrier mounted within said barrel and seated on said lip and retained in place by frictional sealing engagement between the outer diameter of said carrier and the inner wall of said barrel, said needle carrier having an extension protruding through the opening at the lower end of said barrel;
   - internal shoulders extenting inwardly on the inner wall of said barrel directly above said carrier to aid in retaining said carrier in place during use;
   - a hypodermic needle mounted on said extension;
   - a plunger slidably mounted in said barrel through the upper open end and defining a fluid chamber between said carrier and said plunger;
   - a central bore through said carrier and extension for fluid communication between said needle and said chamber;
   - an enlarged bore in said carrier near said chamber and coaxial with said central bore;
   - a shaft extending from the lower end of said plunger;
   - a hub on the lower end of said shaft adapted to lock into said enlarged bore;and
   - expansion means on said plunger to deform said shoulders and release said carrier when said hub engages said enlarged bore.

2. The hypodermic syringe of claim 1 wherein said shaft is shearable above said hub to allow said hub to be broken off and left in said bore after use.

3. The hypodermic syringe of claim 1 further comprising a plunger seal member secured about said shaft between said plunger and said hub.

4. The hypodermic syringe of claim 3 further comprising at least one shoulder about said shaft to retain said seal about said shaft.

* * * * *